United States Patent
Hao et al.

(10) Patent No.: US 9,757,320 B2
(45) Date of Patent: Sep. 12, 2017

(54) ORAL CARE COMPOSITION

(71) Applicant: Colgate-Palmolive Company, New York, NY (US)

(72) Inventors: Zhigang Hao, Bridgewater, NJ (US); Ying Yang, Monmouth Junction, NJ (US); Zhiqiang Liu, Bridgewater, NJ (US); Xu Guofeng, Plainsboro, NJ (US); Paul Joseph Vincenti, Jefferson, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/652,780

(22) PCT Filed: Dec. 19, 2012

(86) PCT No.: PCT/US2012/070497
§ 371 (c)(1),
(2) Date: Jun. 16, 2015

(87) PCT Pub. No.: WO2014/098817
PCT Pub. Date: Jun. 26, 2014

(65) Prior Publication Data
US 2016/0008254 A1    Jan. 14, 2016

(51) Int. Cl.
| | | |
|---|---|---|
| A61Q 11/00 | (2006.01) | |
| A61K 8/58 | (2006.01) | |
| A61K 8/27 | (2006.01) | |
| A61K 8/55 | (2006.01) | |
| A61K 8/67 | (2006.01) | |
| A61K 33/30 | (2006.01) | |

(52) U.S. Cl.
CPC .................. *A61K 8/58* (2013.01); *A61K 8/27* (2013.01); *A61K 8/55* (2013.01); *A61K 8/676* (2013.01); *A61K 33/30* (2013.01); *A61Q 11/00* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 5,059,416 A | 10/1991 | Cherukuri et al. | |
| 6,420,419 B1 * | 7/2002 | Suzuki | A61K 31/665 514/474 |
| 8,337,818 B2 | 12/2012 | Lin et al. | |
| 8,617,523 B2 | 12/2013 | Trivedi et al. | |
| 8,858,920 B2 | 10/2014 | Robinson et al. | |
| 2005/0271602 A1 | 12/2005 | Milanovich et al. | |
| 2007/0053851 A1 | 3/2007 | Maillan et al. | |
| 2007/0183989 A1 | 8/2007 | Prencipe et al. | |
| 2009/0214628 A1 * | 8/2009 | de Rijk | A01N 59/00 424/450 |
| 2011/0280855 A1 | 11/2011 | Levin | |
| 2012/0052025 A1 | 3/2012 | Porter et al. | |
| 2013/0224270 A1 | 8/2013 | Robinson et al. | |

FOREIGN PATENT DOCUMENTS

| | | |
|---|---|---|
| EP | 0884321 | 2/2003 |
| JP | S63-141921 A | 6/1988 |
| JP | 2000-351905 A | 12/2000 |
| TW | 201034697 | 10/2010 |
| WO | WO 02/058662 | 8/2002 |
| WO | WO 02/089756 | 11/2002 |
| WO | WO 2004/041228 | 5/2004 |
| WO | WO 2004/110164 | 12/2004 |
| WO | WO 2006/052762 | 5/2006 |
| WO | WO 2007/027314 | 3/2007 |
| WO | WO 2007/099398 | 9/2007 |
| WO | WO 2010/074025 | 7/2010 |
| WO | WO 2011/116216 | 9/2011 |
| WO | WO 2011/124573 | 10/2011 |
| WO | WO 2012/086342 | 6/2012 |
| WO | WO 2012/136574 | 10/2012 |

OTHER PUBLICATIONS

International Search Report and Written Opinion in International Application No. PCT/US2012/070497, mailed Sep. 27, 2013.
Written Opinion in International Application No. PCT/US2012/070497, 7, mailed Nov. 25, 2014.
Clarke, 2001, Clinical and Microbiological Effects of Oral Zinc Ascorbate Gel in Cats, J. Vet. Dentistry 18(4):177-183.

* cited by examiner

*Primary Examiner* — Lezah Roberts

(57) ABSTRACT

Provided herein is an oral care composition comprising an orally-acceptable aqueous vehicle and an antimicrobial ingredient, wherein the antimicrobial ingredient comprises a zinc ascorbylphosphate and methods for treating or preventing a disease or disorder of the oral cavity using the oral care compositions disclosed herein.

10 Claims, No Drawings

ORAL CARE COMPOSITION

BACKGROUND OF THE INVENTION

Oral bacteria are known to cause various diseases or disorders of the oral cavity, including dental caries, periodontal diseases such as gingivitis and periodontitis, plaque, oral malodour and halitosis. Oral bacteria, and the chronic inflammation of oral tissues which they cause, have also been implicated in a number of systemic diseases, including cardiovascular diseases.

It is therefore desirable to provide oral care compositions comprising antibacterial agents. Many antibacterial agents have been utilised previously, with varying degrees of success. Zinc compounds, in particular zinc oxide, have shown significant promise. In addition to their antimicrobial properties, zinc compounds can fight plaque, prevent calculus formation and reduce mouth malodour. Zinc compounds have also been used in the treatment and prevention of other oral conditions such as pyorrhea and tooth hypersensitivity.

In spite of these promising properties, the use of zinc in oral care compositions has nevertheless been limited. Many antimicrobial zinc compounds, and in particular zinc oxide, suffer from poor aqueous solubility. This restricts the range of formulations into which the zinc compounds of the prior art may be incorporated. Poor solubility may lead to difficulties in achieving a uniform product during the manufacture of oral care formulations. There is therefore a need in the art for zinc compounds with improved solubility.

It is generally desirable to provide antimicrobial ingredients with high potency. Potency may be quantified by minimum inhibitory concentration (MIC) measurements. The MIC is the minimum concentration needed to produce a biocidal or biostatic effect. As zinc has been reported to have undesirable organoleptic properties and can cause mouth irritation, there is a need in the art for zinc compounds with improved potency to allow lower dosages of zinc to be used whilst maintaining the useful functionality of the zinc.

BRIEF SUMMARY OF THE INVENTION

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

An aim of the present invention is to provide an oral care composition which contains a zinc compound with improved solubility in aqueous media and enhanced antimicrobial potency.

In a first aspect, the present invention provides an oral care composition comprising an orally-acceptable aqueous vehicle and an antimicrobial ingredient, wherein the antimicrobial ingredient comprises a zinc ascorbylphosphate.

Optionally, the zinc ascorbyl phosphate is selected from the group consisting of: ascorbylphosphato zinc (II), zinc ascorbylphosphatochlorido zinc (II), ascorbylphosphatohydroxo zinc (II), and mixtures thereof.

Optionally, the zinc ascorbylphosphate is in the composition at a concentration of at least 3.0 mM.

Optionally, the pH of the composition is in the range 5.5 to 10, preferably 6 to 8.

Optionally, the composition further comprises at least one component selected from the group consisting of surfactants, desensitising agents, whitening agents, tartar control agents, abrasives, binders, thickeners, detergents, adhesion agents, foam modulators, pH modifying agents, mouth feel agents, sweeteners, flavourings, colorants, preservatives, humectants, fluoride ion sources and combinations thereof.

Optionally, the composition is in the form of a dentifrice.

Optionally, the composition is in the form of a mouth rinse.

Optionally, the composition is for use in a method of treatment or preventing a disease or disorder of the oral cavity in a human or animal subject, which method comprises applying the composition to the oral cavity of the subject.

In a second aspect, the invention provides use of zinc ascorbylphosphate as an antimicrobial ingredient in an oral care composition.

In a third aspect, the invention provides a method of treating or preventing a disease or disorder of the oral cavity in a human or animal subject, which method comprises applying the composition of the invention to the oral cavity of the subject.

In a fourth aspect, the invention provides an oral care kit comprising an oral care composition comprising zinc ascorbylphosphate.

In a fifth aspect, the invention provides a method of manufacturing an oral care composition comprising preparing a suspension of zinc oxide; preparing a solution of ascorbyl phosphate; mixing the zinc oxide suspension and the ascorbyl phosphate solution; and reacting the zinc oxide with ascorbyl phosphate so as to form a complex.

It has surprisingly been found that zinc ascorbylphosphate has significantly higher solubility and antimicrobial potency in comparison to antimicrobial ingredients of the prior art.

DETAILED DESCRIPTION OF THE INVENTION

The following description of the preferred embodiment(s) is merely exemplary in nature and is in no way intended to limit the invention, its application, or uses.

The oral care compositions of the invention include zinc ascorbylphosphate, which functions as an antimicrobial ingredient, and an orally-acceptable aqueous vehicle. Zinc ascorbylphosphate has been surprisingly found to be more soluble in aqueous media than the zinc compounds conventionally used in oral care compositions. Improved solubility is generally desirable as it allows the formulator greater flexibility as well as reducing manufacturing difficulties. Zinc ascorbylphosphate has also been found to have exceptionally good antimicrobial properties and antioxidant properties that promote the well-being of oral cavities. This may allow the quantity of zinc in oral care compositions to be reduced, thereby reducing consumer perception of the negative organoleptic properties of zinc, while still delivering its desirable functionality. It is also desirable from a commercial standpoint to reduce the amount, and hence the cost, of active ingredients in oral care compositions.

The term "zinc ascorbylphosphate" generally refers to any complex which comprises a zinc center and at least one ascorbylphosphate ligand.

Zinc ascorbylphosphate may optionally comprise one or more additional ligands. The nature of the additional ligands is not particularly limited, provided that the resulting complex is suitable for use in an oral care composition. Examples of preferred additional ligands include hydroxo and chlorido ligands, halides (e.g., fluoro, bromo, iodo) and organic anions (e.g., acetate, formate and nitrate.)

Preferably, the zinc ascorbylphosphate is a zinc ascorbylphosphate obtained from, or obtainable by, the process of:
a. preparing an aqueous suspension of zinc oxide;
b. preparing an aqueous solution of ascorbyl phosphate;
c. mixing the zinc oxide suspension and the ascorbyl phosphate solution;
d. optionally adjusting the pH of the mixture, preferably wherein the pH of the solution is adjusted to pH 7 and/or preferably wherein the pH of the solution is adjusted using an acid such as hydrochloric acid; and
e. preferably allowing the resulting solution to stand until a clear solution is obtained.

Without wishing to be bound by a particular theory, it is believed that the above process produces a mixture of zinc complexes. When analysed by LC-MS-MS, the mixture of complexes appears principally to comprise ascorbylphosphato zinc (II), ascorbylphosphatochlorido zinc (II) and ascorbylphosphatohydroxo zinc (II). Other minor components could be present.

Preferably, the zinc ascorbylphosphate is a zinc ascorbylphosphate selected from the group consisting of: ascorbylphosphato zinc (II), ascorbylphosphatochlorido zinc (II), ascorbylphosphatohydroxo zinc (II) and mixtures thereof.

More preferably, the zinc ascorbylphosphate is a mixture of ascorbylphosphato zinc (II), ascorbylphosphatochlorido zinc (II) and ascorbylphosphatohydroxo zinc (II). The ratio of two of the three ingredients against the other is 1:6 to 6:1. Preferably, the ratio of ascorbylphosphato zinc (II):ascorbylphosphatochlorido zinc (II):ascorbylphosphatohydroxo zinc (II) is 3:5:1.

An orally-acceptable aqueous vehicle is any mixture which includes water and an oral care component. The nature of the oral care component is not particularly limited. The oral care component may, for example, be selected from the group consisting of: surfactants, desensitising agents, whitening agents, tartar control agents, abrasives, binders, thickeners, detergents, adhesion agents, foam modulators, pH modifying agents, mouth feel agents, sweeteners, flavorants, colorants, preservatives, humectants, fluoride ion sources and combinations thereof. Preferably, the orally-acceptable aqueous vehicle comprises a fluoride ion source and/or a humectant. Preferably, the zinc ascorbyl phosphate is soluble in the orally-acceptable aqueous vehicle. The orally-acceptable aqueous vehicle may optionally comprise one or more co-solvents. The co-solvent may be, for example, ethanol. Additionally, the co-solvent may be glycerine or propylene glycol.

The oral care compositions described herein may be formulated into any delivery form known in the art. For example, the compositions may be formulated into a mouth rinse, a paste, a gel, a lozenge, (dissolvable or chewable), a spray, a gum or a film (wholly or partially dissolvable or indissoluble). The composition may contain any conventional excipients or carriers. The excipient will of course vary depending on the dosage form or means of dosage selected.

Preferably, the oral care compositions may be formulated as a dentifrice. Examples of dentifrices include toothpastes and gels. Preferably, the dentifrice is formulated for use in brushing the teeth. When formulated as a dentifrice, the composition preferably comprises a fluorine or fluoride compound.

Alternatively, the compositions of the present invention may be formulated as a mouth rinse. A mouth rinse typically comprises an aqueous or alcoholic solution of one or more oral care ingredients.

Typically, the oral care composition will comprise at least an effective amount of zinc ascorbyl phosphate. An effective amount is an amount which inhibits the growth of at least one microorganism, or which provides a biocidal effect. The microorganism is typically a bacterium. Preferably, the microorganism is a microorganism found in the oral cavity. More preferably, the microorganism is a disease-causing microorganism found in the oral cavity.

Preferably, the oral care composition comprises zinc ascorblyphosphate at a concentration of at least 3.0 mM, or at least 3.5 mM, or at least 4.0 mM, or at least 4.5 mM, or at least 5.0 mM, or at least 6.0 mM.

Typically, the oral care composition will comprise less than the maximum safe concentration of zinc ascorbylphosphate. The maximum safe concentration is the highest concentration which may be incorporated into the oral care composition without cause permanent harm to a subject when the oral care composition is administered to the subject. Preferably, the oral care compositions contain less than the concentration of zinc ascorbylphosphate which can be perceived by a typical consumer. Preferably, the concentration of zinc ascorbylphosphate does not exceed the thermodynamic solubility of zinc ascorbylphosphate in the composition.

The oral care compositions may comprise zinc ascorbylphosphate at a concentration no greater than 50 mM, or 10 mM, or 5 mM, or 3 mM.

Preferably, the zinc ascorbyl phosphate may be in the composition at a concentration in the range 3 mM to 5 mM. More preferably, the zinc ascorbyl phosphate is present in the composition at a concentration in the range 3 mM to 4 mM. Optionally, the zinc ascorbyl phosphate may be in the composition at a concentration of 3 mM, or 3.5 mM, or 4.0 mM, or 4.5 mM, or 5.0 mM, or 5.5 mM, or 6.0 mM.

It will be appreciated that the concentration of the zinc ascorbyl phosphate in the composition will vary depending on the nature of the composition. Typically, the pH of the composition will be in the range pH 2 to pH 10. Optionally, the pH of the composition will be in the range pH 2 to pH 8, or pH 3 to pH 8, or pH 4 to pH 8, or pH 5 to pH 7, or pH 6 to pH 10 or pH 7 to pH 9. A preferred range for the concentration of zinc ascorbylphosphate in a dentifrice is 0.05 to 4% by weight of the composition. A preferred range for the concentration of zinc ascorbylphosphate in a mouth rinse composition is 0.05 to 2% by weight of the composition.

The composition may have any pH which is acceptable for use in an oral care composition. Preferably, the pH of the composition is in the range of pH 5.5 to pH 10. More preferably, the pH of the composition is in the range of pH 6 to pH 8. Still more preferably, the pH is in the range of pH 6.5 to pH 7.4. Most preferably, the pH of the composition is pH 7.

The compositions of the present invention may comprise one or more additional oral care ingredients. The one or more additional oral care ingredients may optionally be selected from the group consisting of: surfactants, desensitising agents, whitening agents, tartar control agents, abrasives, binders, thickeners, detergents, adhesion agents, foam modulators, pH modifying agents, mouth feel agents, sweeteners, flavorants, colorants, preservatives, humectants, fluoride ion sources and combinations thereof.

Surfactants may be used in the oral care compositions of the present invention to provide foaming, taste, flavour, texture and mouth feel properties to the compositions, and in particular to render the compositions more cosmetically acceptable. Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine. Preferably, the surfactant comprises sodium lauryl sulfate (SLS).

The composition of the present invention optionally incorporates one or more desensitizing agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., in amounts in the range from 1 wt % to 20 wt % by weight based on the total weight of the composition, depending on the agent chosen. The compositions of the present invention may also be used to treat hypersensitivity by blocking dentin tubules when applied to a tooth.

The compositions of the present invention may optionally include a tooth whitening or tooth bleaching agent. Suitable whitening and bleaching agents include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., in amounts in the range from 1 wt % to 20 wt % by weight based on the total weight of the composition, depending on the agent chosen.

The oral care compositions of the present invention may optionally include tartar control agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ sodium tripolyphosphate, long chain polyphosphates such as sodium hexametaphosphate and cyclic phosphates such as sodium trimetaphosphate.

The compositions of the present invention may also include an abrasive. The abrasive may be a silica abrasive such as precipitated or hydrated silicas having a mean particle size of up to about 20 microns, such as Zeodent 105 and Zeodent 114 marketed by J.M. Huber Chemicals Division, Havre de Grace, Md. 21078, or Sylodent 783 marketed by Davison Chemical Division of W.R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Other possible abrasive materials include silica gels and precipitated amorphous silica having an oil absorption value of less than 100 cc/100 g silica and optionally in the range of from 45 cc/100 g to less than 70 cc/100 g silica. These silicas are colloidal particles having an average particle size ranging from 3 microns to 12 microns, and optionally between 5 to 10 microns and a pH range from 4 to 10 optionally 6 to 9 when measured as a 5% by weight slurry.

The abrasive may optionally be present in an amount in the range from 15 to 35 wt % based on the weight of the composition, optionally 20 to 30 wt % based on the weight of the composition.

The compositions of the invention may contain a binder. Any conventional binder may be utilized. Suitable agents include marine colloids, carboxyvinyl polymers, carrageenans, starches, cellulosic polymers such as hydroxyethylcellulose. carboxymethylcellulose (carmellose), hydroxypropyl methyl cellulose and salts thereof (e.g., carmellose sodium), natural gums such as karaya, xanthan, gum arabic and tragacanth, chitosan, colloidal magnesium aluminum silicate, and colloidal silica. Preferably, if the composition is a dentifrice then a binder is present in the composition in an amount in the range 0.5% to 5% by weight of the composition.

Thickening agents suitable for use in the compositions of the present invention include natural and synthetic gums and colloids. Suitable thickening agents include naturally occurring polymers such as carrageenan, xanthan gum, polyglycols of varying molecular weights sold under the tradename Polyox, and polyvinylpyrrolidone. Compatible inorganic thickening agents include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickening agents include natural and synthetic clays such as hectorite clays, lithium magnesium silicate (laponite) and magnesium aluminum silicate (Veegum).

The oral care compositions of the present invention may optionally comprise one or more adhesion agents. The adhesion agent may by a polymeric adherent material. The polymeric adherent material may be any known or to be developed in the art that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), carboxymethyl cellulose (CMC).

Preferably, the polymeric adherent material comprises at least one cellulose material, for example sodium carboxymethyl cellulose.

The polymeric adherent material may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)—propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). Optionally, the copolymer may be selected from the group consisting of: poly (methylvinylether/maleic anhydride), or poly (methylvinylether/maleic acid), or poly (methylvinylether/maleic acid) half esters, or poly (methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

The oral care compositions of the invention also may include a foam modulator. Foam modulators typically increase the amount of foam produced, for example, when the oral cavity is brushed using the composition of the present invention.

Illustrative examples of foam modulators that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of 200,000 to 7,000,000, and preferably 600,000 to 2,000,000 and more preferably 800,000 to 1,000,000.

The polyoxyethylene may be present in an amount of 1% to 90%, in one embodiment 5% to 50% and in another embodiment 10% to 20% by weight of the oral care carrier component of the oral care compositions of the present invention. The dosage of foaming agent in the oral care composition (i.e., a single dose) is 0.01 to 0.9% by weight, 0.05 to 0.5% by weight, and in another embodiment 0.1 to 0.2% by weight.

Optionally, the compositions of the present invention comprise at least one pH modifying agent. Such agents include acidifying agents to lower pH, basifying agents to raise pH, and buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

Mouth-feel agents that may be used herein include materials which impart a desirable texture or other feeling during use of the composition. Such agents include bicarbonate salts, which may impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate, and mixtures thereof. One or more bicarbonate salts are optionally present in a total amount in the range of 0.1% to 50%, for example 5% to 20% by weight.

The compositions of the present invention may optionally comprise a sweetener. Sweeteners which may be used in the compositions of the present invention include artificial sweeteners such as saccharin, acesulfam, neotam, cyclamate or sucralose; natural high-intensity sweeteners such as thaumatin, stevioside or glycyrrhizin; or sugar alcohols such as sorbitol, xylitol, maltitol or mannitol. These may be present in amounts in the range of 0 wt % to 0.2 wt %, optionally 0.005 wt % to 0.1 wt % based on the weight of the composition.

The compositions of the present invention may optionally comprise a flavorant. Flavorants that may be used in the compositions of the present invention include essential oils as well as various flavoring aldehydes, esters, alcohols, and similar materials. Examples of the essential oils include oils of spearmint, peppermint, aniseed, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint. The flavorant may be incorporated in the oral care composition at a concentration in the range of 0.1 to 5 wt % and typically 0.5 to 1.5 wt %.

If the oral care composition is formulated as a mouth rinse, flavorants are preferably used in an amount in the range of 0 wt % to 0.5 wt %, optionally 0.03 wt % to 0.3 wt % based on the weight of the composition.

If the oral care composition is formulated as a dentifrice or a tooth gel, flavorants are preferably present in the composition in an amount in the range of 0.1 to 5 wt %, optionally 0.5 to 1.5 wt % based on the weight composition.

A composition of the invention may comprise at least one colorant. Colorants herein include pigments, dyes, lakes and agents imparting a particular luster or reflectivity such as pearling agents. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount in the range of from 0.001 wt % to 20 wt %, for example, from 0.01 wt % to 10 wt %, or from 0.1 wt % to 5 wt %, by total weight of the composition.

Preservatives, such as chlorhexidine, triclosan, quaternary ammonium compounds (such as benzalkonium chloride) or parabens (such as methyl or propyl paraben) may be used in the compositions. The amount of preservative is typically in the range from 0 to 0.5 wt %, optionally 0.05 to 0.1 wt % based on the weight of the composition.

The compositions of the present invention may optionally comprise a humectant. Any orally acceptable humectant can be used, including without limitation, polyhydric alcohols such as glycerin, sorbitol, xylitol or low molecular weight PEGs. Most humectants also function as sweeteners. One or more humectants are optionally present in a total amount in the range of from 1 wt % to 70 wt %, for example, from 1 wt % to 50 wt %, from 2 wt % to 25 wt %, or from 5 wt % to 15 wt %, by total weight of the composition.

Preferably, the composition comprises a fluoride ion source. Fluoride ion sources include, but are not limited to: stannous fluoride, sodium fluoride, potassium fluoride, potassium monofluorophosphate, sodium monofluorophosphate, ammonium monofluorophosphate, sodium fluorosilicate, ammonium fluorosilicate, amine fluoride such as olaflur (N'-octadecyltrimethylendiamine-N,N,N'-tris(2-ethanol)-dihydrofluoride), ammonium fluoride, and combinations thereof. Optionally, the fluoride ion source includes stannous fluoride, sodium fluoride, amine fluorides, sodium monofluorophosphate, as well as mixtures thereof. Preferably, the oral care composition of the invention may also contain a source of fluoride ions or fluorine-providing ingredient in amounts sufficient to supply 50 to 5000 ppm fluoride ion, e.g., from 100 to 1000, from 200 to 500, or 250 ppm fluoride ion. Fluoride ion sources may be added to the compositions of the invention at a level in the range of 0.001 wt % to 10 wt %, e.g., from 0.003 wt % to 5 wt %, 0.01 wt % to 1 wt, or 0.05 wt %. However, it is to be understood that the weights of fluoride salts to provide the appropriate level of fluoride ion will obviously vary based on the weight of the counter ion in the salt, and one of skill in the art may readily determine such amounts. A preferred fluoride salt may be sodium fluoride.

Also provided is a method of treating or preventing a disease or disorder of the oral cavity in a human or animal subject, which method comprises applying an oral care composition comprising zinc ascorbylphosphate to the oral cavity of the subject.

Preferably, the subject is a human, or a companion animal such as a cat, a dog or a horse. Most preferably, the subject is a human. The composition may be applied by any suitable method known in the art. The composition may be applied to the oral cavity of the subject using any suitable technique known in the art. The technique may vary depending on the nature of the composition. For example, if the composition is a dentifrice it is preferably applied by brushing and more preferably by brushing for about 2 minutes.

Any appropriate dosage regime may be used in combination with the method of the present invention. For example, the composition may be applied to the oral cavity of the subject once a day, twice a day, or more often. Preferably, the composition is applied to the oral cavity of the subject twice a day. The subject may be treated with the composition for a period of at least one day, at least one month, at least six months, at least one year, or for a lifetime.

Various diseases and disorders of the oral cavity may be treated or prevented using the methods and compositions of the present invention. Optionally, the methods and compositions of the present invention may be used to treat or prevent a chronic disease or disorder. The disease or disorder may be dental caries. The disease or disorder may be a periodontal disease, or periodontal inflammation. The periodontal disease may be gingivitis. The disease or disorder may be halitosis.

The disease or disorder may be tooth hypersensitivity. If the disease or disorder is tooth hypersensitivity, the composition preferably comprises an additional oral care ingredient which is a desensitizing agent. The disease or disorder may be the buildup of tartar and/or calculus formation. If the disease or disorder is the buildup of tartar and/or calculus formation, the composition preferably comprises an additional oral care ingredient which is a tartar control agent and/or an abrasive.

Optionally, the disease or disorder may be tooth discoloration. If the disease or disorder is tooth discoloration, the composition preferably comprises an additional oral care ingredient which is a tooth whitening agent.

In a further aspect, the present invention provides an oral care kit comprising an oral care composition, which composition comprises zinc ascorbylphosphate. The kits of the present invention preferably comprise the composition of the invention disposed in appropriate packaging. The kits of the invention may optionally comprise a suitable applicator, such as a toothbrush or the like. The kits of the invention may optionally comprise means for measuring an appropriate dosage the composition. If the composition is a mouth rinse, the means for the measuring and appropriate dosage of the composition preferably comprises a graduated measuring vessel.

In a further aspect, the invention provides a method for manufacturing an oral care composition. The method comprises producing zinc ascorbylphosphate. The zinc ascorbylphosphate may then be incorporated into an oral care composition using any suitable method known in the art.

Preferably, the step of producing zinc ascorbylphosphate comprises:
a. preparing a suspension, preferably an aqueous suspension, of zinc oxide;
b. preparing a solution, preferably an aqueous solution, of ascorbyl phosphate;
c. mixing the zinc oxide suspension and the ascorbyl phosphate solution;
d. optionally adjusting the pH of the mixture, preferably wherein the pH of the solution to pH 7 and/or preferably wherein the pH of the solution is adjusted using hydrochloric acid; and
e. reacting the zinc oxide with the ascorbyl phosphate, preferably by allowing the mixture to stand until a clear solution is obtained.

Optionally, liquid chromatography may be used to monitor the process for producing zinc ascorbylphosphate.

Preferably, the zinc oxide suspension contains 10 to 20 mg/mL zinc oxide. The zinc ascorbylphosphate solution preferably comprises between 50 and 70 mg/mL ascorbylphosphate.

The pH of the mixture of zinc oxide and ascorbyl phosphate may be adjusted using any acid or base which is compatible with oral care formulations. Preferably, the pH is adjusted with acid. The acid is preferably hydrochloric acid. It is believed that varying the pH of the solution and/or the reagent used to adjust the pH will vary the composition of the resulting zinc ascorbylphosphate.

Additional ligands may be incorporated into the zinc ascorbylphosphate using any appropriate method known in the art.

EXAMPLES

Example 1

Synthesis and Characterization of Zinc Ascorbylphosphate Complexes

Zinc ascorbyl phosphate complexes were synthesized by mixing an aqueous suspension of zinc oxide with an aqueous solution of ascorbyl phosphate and adjusting the pH of the resulting mixture to about 7.0. The composition of the resulting solution was investigated by liquid chromatography and mass spectrometry. A mixture of three zinc ascorbyl phosphate complexes was formed. The mixture was soluble in water at a concentration of 0.08 mM.

Materials and Methods: A suspension of zinc oxide (162 mg) was prepared in deionized water (10 ml). A solution of ascorbyl phosphate (646 mg) in deionized water (10 ml). An aliquot of the zinc oxide suspension (1 ml) was mixed with an aliquot of the ascorbyl phosphate solution (1 ml). The pH of the resulting mixture was adjusted to about 7.0 using 1 N hydrochloric acid. The solution was then allowed to stand at room temperature for approximately 3 hours, until a clear solution was obtained. A sample of the clear solution was analyzed using liquid chromatography electro spray ionization-tandem mass spectrometry (LC-ESI-MSMS).

LC analysis was performed using a TSQ quantum tandem mass spectrometer (Thermo-Electron Company, San José, Calif., USA) equipped with an ESI interface and Agilent 1100 capillary LC system (model Agilent 1100, Agilent Technologies, Palo Alto, Calif., USA).

The capillary LC system was equipped with a capillary binary pump (model G1376A), a diode array detector (model 1315B), a micro vacuum degasser and a thermostatted column compartment (model G1316A). The capillary pump was set to the micro-flow mode. The LC separation was achieved using an Atlantis HILIC column 2.1 mm in diameters and 50 mm in length containing particles 5 μm in size (Waters Corporation, Milford, Mass., USA, Part No. 186002012). The mobile phase was composed of 15% water and 85% methanol. The flow rate was 100 μL per minute and the injected volume was 1 μL.

The TSQ quantum tandem mass spectrometer was operated in the negative-ion mode under the following conditions: nitrogen (>99.99% purity) was used as the sheath gas and as the auxiliary gas at pressures of 35 psi and 5 units, respectively. The ESI spray voltage was 4.5 kV. The temperature of the heated capillary was maintained at 350° C. The MS screen range was from 80 to 1200 m/z. Data were acquired using the Xcalibur software system (Thermo-Electron Company, San Jose, Calif., USA).

Results and Discussion:

Based on the mass spectra, it is believed that three zinc complexes were produced. Complex 1 is ascorbylphosphato zinc (II). Complex 2 is ascorbylphosphatochlorido zinc (II). Complex 3 is ascorbylphosphatohydroxo zinc (II).

Example 2

Bio Activity of Zinc Ascorbyl Phosphate Complexes

The minimum inhibitory concentration of the mixture of complexes obtained in Example 1 was determined. The mixture of zinc ascorbyl phosphate complexes was found to have a lower minimum inhibitory concentration than zinc oxide alone, ascorbyl phosphate alone, and a conventional antimicrobial ingredient used in oral care compositions, a zinc-lysine complex.

Materials and Methods

Stock solutions of the zinc ascorbyl phosphate of Example 1, ascorbyl phosphate, zinc oxide, and the zinc-lysine complex were each prepared in water. The concentration of active ingredient in each solution was 0.1 M. Aliquots of each test solution (200 μL) were placed in the first row of a 96 well plate. Serial dilutions of the stock solutions were prepared on the plate by mixing the stock solutions with tryptic soy broth on a 1:1 basis. The concentrations of active ingredient prepared on this basis varied from 50 mM to 0.00488 mM.

A solution of *A. viscuosus* with an optical density of 0.2 at 610 nm was prepared. Aliquots of the *A. viscuosus* solution (100 μL) were then added to each test well. Four control wells containing TSB buffer and *A. viscuosus* solution were prepared. Four blank wells containing TSB buffer alone were also prepared.

The plate was then incubated at 37° C. for 18 hours. The optical density of each well at 610 nm was then recorded using a plate reader.

Results And Discussion

Table 1 shows the optical density readings obtained for each of the compounds investigated. A lower optical density reading correlates to a lower concentration of bacteria, and hence an improved antibacterial effect.

TABLE 1

| Concentration of active ingredient/ mM | Ascorbyl Palmitate | Zinc Oxide | Zinc-Lysine Complex | Zinc Ascorbyl Phosphate | Media Control | Bacteria Control |
|---|---|---|---|---|---|---|
| 50 | 0.64 | 1.55 | 0.56 | 0.32 | 0.04 | 0.73 |
| 25 | 0.68 | 0.65 | 0.35 | 0.14 | 0.04 | 0.71 |
| 12.5 | 0.72 | 0.40 | 0.20 | 0.11 | 0.04 | 0.71 |
| 6.25 | 0.69 | 0.29 | 0.15 | 0.11 | 0.04 | 0.71 |
| 3.125 | 0.68 | 0.33 | 0.34 | 0.32 | | |
| 1.563 | 0.70 | 0.45 | 0.44 | 0.57 | | |
| 0.781 | 0.70 | 0.60 | 0.58 | 0.53 | | |
| 0.391 | 0.69 | 0.66 | 0.65 | 0.62 | | |
| 0.195 | 0.71 | 0.67 | 0.69 | 0.67 | | |
| 0.00977 | 0.71 | 0.68 | 0.71 | 0.68 | | |
| 0.005 | 0.70 | 0.68 | 0.68 | 0.69 | | |

The data show that zinc ascorbylphosphate inhibits bacterial growth when present in an amount of 0.195 mM or greater. Zinc ascorbylphosphate produced a greater effect on antibacterial activity than either ascorbylphosphate or zinc-lysine complex at all concentrations investigated. At concentrations between 0.391 mM and 12.5 mM, zinc ascorbylphosphate produces a greater inhibitory effect than zinc oxide. At a dose of 0.195 mM, zinc ascorbylphosphate produced an inhibitory effect which was approximately equal to that of zinc oxide.

Zinc oxide is poorly soluble under aqueous conditions. Suspensions of solid particles in liquids tend to have high apparent absorbance values due to light scattering by the solid particles. The anomalously high optical density readings observed for the solutions at concentrations of 25 mM and above are therefore consistent with the presence of a solid precipitate.

Zinc ascorbylphosphate shows a positive dose response, that is, an increase in antibacterial effect with concentration. It is believed that no increase in antibacterial effect would be observed for zinc oxide once the concentration of zinc oxide exceeds the solubility limit. It is therefore believed that zinc ascorbylphosphate will show a greater inhibition of bacterial growth at high concentrations than zinc oxide.

The presence of insoluble components in oral care compositions can be undesirable, particularly in mouth rinse formulations. Insoluble components can cause, for example, processing difficulties and variations in the dose of active ingredient delivered when the compositions are used in a method for treating a subject. Zinc ascorbylphosphate will therefore have a greater useful dosage range than zinc oxide due to its improved solubility.

An exemplary dentifrice of the present invention, comprising zinc ascorbylphosphate as a pure compound or mixture, is described in Table 2.

TABLE 2

| INGREDIENT | WEIGHT % |
|---|---|
| PEG600 | 3 |
| CMC-7 | 0.65 |
| Xanthan | 0.2 |
| Sorbitol | 27 |
| Glycerin | 20 |
| Saccharin | 0.3 |
| Tetrasodium pyrophosphate | 0.5 |
| Calcium pyrophosphate | 0.25 |
| Sodium phosphate dibasic | 3.5 |
| Sodium fluoride | 0.32 |
| Titanium dioxide | 0.5 |
| Abrasive silica | 8 |

TABLE 2-continued

| INGREDIENT | WEIGHT % |
| --- | --- |
| Thickener silica | 8 |
| Sodium lauryl sulfate | 1.5 |
| Flavoring | 1.2 |
| zinc ascorbylphosphate | 2 |
| Water | QS |

An exemplary mouth rinse formulation of present invention, comprising zinc ascorbylphosphate as a pure compound or mixture, is described in Table 3.

TABLE 3

| INGREDIENT | WEIGHT % |
| --- | --- |
| Sorbitol | 5.5 |
| Glycerin | 7.5 |
| Propylene glycol | 7 |
| Sodium saccharin | 0.02 |
| Citric acid (anhydrous) | 0.05 |
| zinc ascorbylphosphate | 0.1 |
| Flavor/dye | 0.12 |
| Potassium sorbate | 0.05 |
| Cocamidopropyl betaine | 1 |
| Water | QS |
| TOTAL | 100 |

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

We claim:

1. An oral care composition comprising an orally-acceptable aqueous vehicle and an antimicrobial ingredient, wherein the antimicrobial ingredient comprises a complex of ascorbylphosphato zinc (II), ascorbylphosphatochlorido zinc (II) and ascorbylphosphatohydroxo zinc (II); and wherein said complex is in the composition at a concentration of at least 3.0 mM.

2. The composition according to claim 1, wherein said complex is in the composition at a concentration of at least 6.0 mM.

3. The composition of claim 1, wherein the pH of the composition is in the range 6 to 8.

4. The composition of claim 1, further comprising at least one component selected from the group consisting of: surfactants, desensitizing agents, whitening agents, tartar control agents, abrasives, binders, thickening agents, detergents, adhesion agents, foam modulators, pH modifying agents, mouth feel agents, sweeteners, flavorants, colorants, preservatives, humectants, fluoride ion sources and combinations thereof.

5. The composition of claim 1, in the form of a dentifrice.

6. The composition of claim 1, in the form of a mouth rinse.

7. The composition of claim 1, for use in a method of treating or preventing a disease or disorder of the oral cavity in a human or animal subject, which method comprises applying the composition to the oral cavity of the subject.

8. A method of treating or preventing a disease or disorder of the oral cavity in a human or animal subject, which method comprises applying the composition of claim 1 to the oral cavity of the subject.

9. An oral care kit comprising the composition of claim 1.

10. A method of manufacturing an oral care composition comprising the steps of:
preparing suspension of zinc oxide;
preparing a solution of ascorbyl phosphate;
mixing the zinc oxide suspension and the ascorbyl phosphate solution and adjusting the pH using HCl; and
reacting the zinc oxide with the ascorbyl phosphate so as to form a complex.

* * * * *